(12) United States Patent
Kimura et al.

(10) Patent No.: US 7,541,459 B2
(45) Date of Patent: Jun. 2, 2009

(54) METHOD OF PRODUCING AMIDE COMPOUND

(75) Inventors: Keizo Kimura, Kanagawa (JP); Katsuyoshi Yamakawa, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 493 days.

(21) Appl. No.: 11/235,368

(22) Filed: Sep. 27, 2005

(65) Prior Publication Data

US 2006/0069252 A1    Mar. 30, 2006

(30) Foreign Application Priority Data

Sep. 27, 2004    (JP) .............................. 2004-280537

(51) Int. Cl.
*C07D 285/22*    (2006.01)
(52) U.S. Cl. ..................... 544/12; 548/300.1
(58) Field of Classification Search .............. 548/300.1; 544/12
See application file for complete search history.

(56) References Cited

U.S. PATENT DOCUMENTS

| | | | |
|---|---|---|---|
| 4,206,143 A | | 6/1980 | Wenzel et al. |
| 4,549,017 A | | 10/1985 | McEntire et al. |
| 5,021,330 A | * | 6/1991 | Bergthaller et al. ......... 430/544 |
| 5,441,857 A | * | 8/1995 | Odenwalder et al. ........ 430/506 |
| 5,556,987 A | * | 9/1996 | Aoki et al. ............... 548/369.7 |

FOREIGN PATENT DOCUMENTS

| | | |
|---|---|---|
| CS | 268 204 B | 3/1990 |
| JP | 8-81445 A | 3/1996 |
| JP | 9-239270 A | 9/1997 |
| JP | 2000-95741 A | 4/2000 |
| JP | 2001-261625 A | 9/2001 |

OTHER PUBLICATIONS

K.P.C. Vollhardt et al. Organische Chemie, Second edition, VCH, Weinheim, 1995, p. 824-826 and p. 834-836.

* cited by examiner

*Primary Examiner*—Shailendra Kumar
*Assistant Examiner*—Sudhakar Katakam
(74) *Attorney, Agent, or Firm*—Birch, Stewart, Kolasch & Birch, LLP

(57) ABSTRACT

The present invention provides a method of producing a compound represented by the following formula (1) or a compound represented by the following formula (4) or a tautomer thereof, the method including reacting a compound represented by the following formula (2) or a compound represented by the following formula (5) or a tautomer thereof with a compound represented by the following formula (3) or a compound represented by the following formula (6) in the presence of an aluminum alkoxide compound.

10 Claims, No Drawings

METHOD OF PRODUCING AMIDE COMPOUND

CROSS-REFERENCE TO RELATED APPLICATIONS

This application claims priority under 35 USC 119 from Japanese Patent Application No. 2004-280537, the disclosure of which is incorporated herein by reference.

BACKGROUND OF THE INVENTION

1. Field of the Invention

The present invention relates to a method of producing amides and amides containing a hetero ring in their molecules which are useful as photographic couplers, photographic additives, medicines and agricultural chemicals or synthetic intermediates of these compounds.

2. Description of the Related Art

Amides and amides containing a hetero ring in their molecules are useful as photographic couplers, photographic additives, medicines and agricultural chemicals or synthetic intermediates of these compounds. Methods of producing these amides have been studied actively so far.

Generally, amides are produced from corresponding carboxylic acids or esters. Examples of methods of producing amides from esters among these starting materials include (1) a method in which esters are first hydrolyzed into carboxylic acids, which are then converted into acid halides, followed by reacting these acid halides with amines (2) and a method in which esters are condensed directly with amines in the presence of a catalyst. There are many unsatisfactory aspects as an industrial production method in the method (1), such as that the method (1) involves many steps and requires anticorrosive production apparatus. On the other hand, the method (2) is carried out in the presence of a protonic acid or Lewis acid catalyst. Examples of Lewis acids which have been hitherto known include tin compounds (e.g., Japanese Patent Application Laid-Open (JP-A) Nos. 62-67055, 54-138513 and 2000-95741), compounds of elements of group III in the periodic table (e.g., JP-A Nos. 2001-261625 and 9-239270), titanium, iron or zinc compounds (e.g., JP-A No. 8-134041) and indium compounds (for example, "Synthetic Communications", vol. 33, p. 297 (2003)). Also, aluminum chloride and aluminum bromide may be used as the Lewis acid, as disclosed in, for example, "Synthetic Communications", vol. 16, 633 (1986).

The production methods using a protonic acid or these catalysts are unsatisfactory as industrial production methods from the standpoints of low yields and the generation of many byproducts, and solution of these problems has been demanded.

SUMMARY OF THE INVENTION

The present invention has been made in view of the above circumstances and provides a method of producing a compound represented by the following formula (1) and a method of producing a compound represented by the following formula (4) or tautomer thereof.

A first aspect of the present invention is to provide a method of producing a compound represented by the following formula (1), the method including reacting a compound represented by the following formula (2) with a compound represented by the following formula (3) in the presence of an aluminum alkoxide compound.

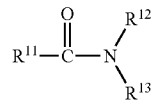

Formula (1)

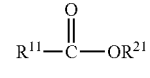

Formula (2)

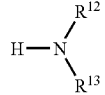

Formula (3)

In the formulae (1), (2) and (3), $R^{11}$ represents a hydrogen atom, an aliphatic group, an aromatic group or a heterocyclic group, $R^{12}$ and $R^{13}$ each independently represent a hydrogen atom, an aliphatic group, an aromatic group or a heterocyclic group and $R^{21}$ represents an aliphatic group, an aromatic group or a heterocyclic group.

A second aspect of the present invention is to provide a method of producing a compound represented by the following formula (4) or a tautomer thereof, the method including reacting a compound represented by the following formula (5) or a tautomer thereof with a compound represented by the formula (6) in the presence of an aluminum alkoxide compound.

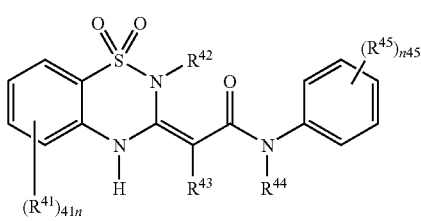

Formula (4)

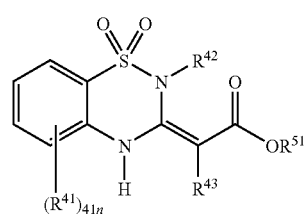

Formula (5)

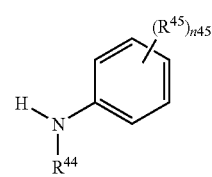

Formula (6)

In the formulae (4), (5) and (6), $R^{41}$ and $R^{45}$ each independently represent a substituent, $R^{42}$, $R^{43}$ and $R^{44}$ each independently represent a hydrogen atom, an aliphatic group, an aromatic group or a heterocyclic group, $R^{51}$ represents an aliphatic group, an aromatic group or a heterocyclic group, $n^{41}$ denotes an integer from 0 to 4, and $n^{45}$ denotes an integer from 0 to 5. When $n^{41}$ is 2 or more, plural $R^{41}$s may be the same or different and may be combined with each other to form a ring. Also, when $n^{45}$ is 2 or more, plural $R^{45}$s may be the same or different and may be combined with each other to form a ring.

DETAILED DESCRIPTION OF THE INVENTION

Embodiments of the present invention will be explained in detail hereinbelow.

In this specification, first the aliphatic group means an alkyl group, substituted alkyl group, alkenyl group, substituted alkenyl group, alkinyl group, substituted alkinyl group, aralkyl group or substituted aralkyl group. The alkyl group may be branched and may form a ring (specifically, for example, a cycloalkyl group). The number of atoms of the alkyl group is preferably 1 to 20, and more preferably 1 to 18. The alkyl part of the substituted alkyl group is the same as the above alkyl group. The alkenyl group may be branched and may form a ring (specifically, for example, a cycloalkenyl group). The number of atoms of the alkenyl group is preferably 2 to 20, and more preferably 2 to 18. The alkenyl part of the substituted alkenyl group is the same as the above alkenyl group. The alkinyl group may be branched and may form a ring (specifically, for example, a cycloalkinyl group). The number of atoms of the alkinyl group is preferably 2 to 20, and more preferably 2 to 18. The alkinyl part of the substituted alkinyl group is the same as the above alkinyl group. Each alkyl part of the aralkyl group and substituted aralkyl group is the same as the above alkinyl group. Each aryl part of the aralkyl group and substituted aralkyl group is the same as the aryl group which will be described later.

Examples of the substituent of substituted alkenyl group, substituted alkinyl group and the alkyl part of the substituted aralkyl group include a halogen atom (e.g., a chlorine atom, bromine atom and iodine atom), alkyl group (represents a straight-chain, branched or cyclic substituted or unsubstituted alkyl group. they include an alkyl group (preferably an alkyl group having 1 to 30 carbon atoms, for example, methyl, ethyl, n-propyl, isopropyl, t-butyl, n-octyl, eicosyl, 2-chloroethyl, 2-cyanoethyl and 2-ethylhexyl), cycloalkyl group (preferably a substituted or unsubstituted cycloalkyl group having 3 to 30 carbon atoms, for example, cyclohexyl, cyclopentyl and 4-n-dodecylcyclohexyl) and, bicyloalkyl group (preferably a bicycloalkyl group having 5 to 30 carbon atoms, specifically a monovalent group obtained by removing one hydrogen atom from bicyloalkane having 5 to 30 carbon atoms, for example, bicyclo [1,2,2] heptane-2-yl and bicyclo [2,2,2] octane-3-yl) and a tricyclo structure having more cyclic structures. The alkyl groups (for example, the alkyl group of an alkylthio group) in the substituent explained below represents an alkyl group having such a concept.), alkenyl group (represents a straight-chain, branched or cyclic substituted or unsubstituted alkenyl group. They include an alkenyl group (preferably a substituted or unsubstituted alkenyl group having 2 to 30 carbon atoms, for example, vinyl, allyl, prenyl, geranyl and oleyl), cycloalkenyl group (preferably a substituted or unsubstituted cycloalkenyl group having 3 to 30 carbon atoms, namely, a monovalent group obtained by removing one hydrogen atom from a cycloalkene having 3 to 30 carbon atoms, for example, 2-cyclopentene-1-yl and 2-cyclohexene-1-yl) and bicycloalkenyl group (a substituted or unsubstituted bicycloalkenyl group, and preferably a substituted or unsubstituted bicyloalkenyl group having 5 to 30 carbon atoms, specifically, a monovalent group obtained by removing one hydrogen atom from a cycloalkene having one double bond, for example, bicyclo[2,2,1]hepto-2-ene-1-yl and bicyclo[2,2,2]octo-2-ene-4-yl)), alkinyl group (preferably a substituted or unsubstituted alkinyl group having 2 to 30 carbon atoms, for example, ethynyl, propargyl and trimethylsilylethynyl group, aryl group (preferably a substituted or unsubstituted aryl group having 6 to 30 carbon atoms, for example, phenyl, p-tolyl, naphthyl, m-chlorophenyl and o-hexadecanoylaminophenyl), heterocyclic group (preferably a monovalent group obtained by removing one hydrogen atom from a five- or six-membered substituted or unsubstituted aromatic or non-aromatic heterocyclic compound, and more preferably a five- or six-membered aromatic heterocyclic group having 3 to 30 carbon atoms, for example, 2-furyl, 2-thienyl, 2-pyrimidinyl and 2-benzothiazolyl), cyano group, hydroxyl group, nitro group, carboxyl group, alkoxy group (preferably a substituted or unsubstituted alkoxy group having 1 to 30 carbon atoms, for example, methoxy, ethoxy, isopropoxy, t-butoxy, n-octyloxy and 2-methoxyethoxy), aryloxy group (preferably a substituted or unsubstituted aryloxy group having 6 to 30 carbon atoms, for example, phenoxy, 2-methylphenoxy, 4-t-butylphenoxy, 3-nitrophenoxy and 2-tetradecanoylaminophenoxy), silyloxy group (preferably a silyloxy group having 3 to 20 carbon atoms, for example, trimethylsilyloxy and t-butyldimethylsilyloxy), heterocyclic oxy group (preferably a substituted or unsubstituted heterocyclic oxy group having 2 to 30 carbon atoms, for example, 1-phenyltetrazole-5-oxy and 2-tetrahydropyranyloxy), acyloxy group (preferably a formyloxy group, substituted or unsubstituted alkylcarbonyloxy group having 2 to 30 carbon atoms or a substituted or unsubstituted arylcarbonyloxy group having 6 to 30 carbon atoms, for example, formyloxy, acetyloxy, pivaloyloxy, stearoyloxy, benzoyloxy and p-methoxyphenylcarbonyloxy), carbamoyloxy group (preferably a substituted or unsubstituted carbamoyloxy group having 1 to 30 carbon atoms, for example, N,N-dimethylcarbamoyloxy, N,N-diethylcarbamoyloxy, morpholinocarbonyloxy, N,N-di-n-octylaminocarbonyloxy and N-n-octylcarbamoyloxy), alkoxycarbonyloxy group (preferably a substituted or unsubstituted alkoxycarbonyloxy group having 2 to 30 carbon atoms, for example, methoxycarbonyloxy, ethoxycarbonyloxy, t-butoxycarbonyloxy and n-octylcarbonyloxy), aryloxycarbonyloxy group (preferably a substituted or unsubstituted aryloxycarbonyloxy group having 7 to 30 carbon atoms, for example, phenoxycarbonyloxy, p-methoxyphenoxycarbonyloxy and p-n-hexadecyloxyphenoxycarbonyloxy), amino group (preferably an amino group, substituted or unsubstituted alkylamino group having 1 to 30 carbon atoms, substituted or unsubstituted anilino group having 6 to 30 carbon atoms, for example, amino, methylamino, dimethylamino, anilino, N-methyl-anilino and diphenylamino), acylamino group (preferably a formylamino group, substituted or unsubstituted alkylcarbonylamino group having 1 to 30 carbon atoms or substituted or unsubstituted arylcarbonylamino group having 6 to 30 carbon atoms, for example, formylamino, acetylamino, pivaloylamino, lauroylamino, benzoylamino and 3,4, 5-tri-n-octyloxyphenylcarbonylamino), aminocarbonylamino group (preferably a substituted or unsubstituted aminocarbonylamino group having 1 to 30 carbon atoms, for example, carbamoylamino, N,N-dimethylaminocarbonylamino, N,N-diethylaminocarbonylamino and morpholinocarbonylamino), alkoxycarbonylamino group (preferably a substituted or unsubstituted alkoxycarbonylamino group having 2 to 30 carbon atoms, for example, methoxycarbonylamino, ethoxycarbonylamino, t-butoxycarbonylamino, n-octadecyloxycarbonylamino, N-methylmethoxycarbonylamino), aryloxycarbonylamino group (preferably a substituted or unsubstituted aryloxycarbonylamino group having 7 to 30 carbon atoms, for example, phenoxycarbonylamino, p-chlorophenoxycarbonylamino and m-n-octyloxyphenoxycarbonylamino), sulfamoylamino group (preferably a substituted or unsubstituted sulfamoylamino group having 0 to 30 carbon atoms, for example, sulfamoylamino, N,N-dimethylaminosulfonylamino and N-n-octylaminosulfonylamino), alkyl or arylsulfonylamino group (preferably a substituted or unsubstituted alkylsulfonylamino having 1 to 30 carbon atoms or a substituted or unsubstituted arylsulfonylamino having 6 to 30 carbon atoms, for example, methylsulfonylamino, butylsulfonylamino, phenylsulfonylamino, 2,3,5-trichlorophenylsulfonylamino and p-methylphenylsulfonylamino), mercapto group, alkylthio group (preferably a substituted or unsubstituted alkylthio group having 1 to 30 carbon atoms, for example, methylthio, ethylthio and n-hexadecylthio), arylthio group (preferably a substituted or unsubstituted arylthio group having 6 to 30 carbon atoms, for example, phenylthio, p-chlorophenylthio and m-methoxyphenylthio), heterocyclic thio group (preferably a substituted or unsubstituted heterocyclic thio group having 2 to 30 carbon atoms, for example, 2-benzothiazolylthio and 1-phenyltetrazole-5-ylthio), sulfamoyl group (preferably a substituted or unsubstituted sulfamoyl group having 0 to 30 carbon atoms, for example, N-ethylsulfamoyl, N-(3-dodecyloxypropyl)sulfamoyl, N,N-dimethylsulfamoyl, N-acetylsulfamoyl, N-benzoylsulfamoyl, N-(N'-phenylcarbamoyl)sulfamoyl), sulfo group, alkyl or arylsulfinyl group (preferably a substituted or unsubstituted alkylsulfinyl group having 1 to 30 carbon atoms or arylsulfinyl group having 6 to 30 carbon atoms, for example, methylsulfinyl, ethylsulfinyl, phenylsulfinyl and p-methylphenylsulfinyl), alkyl or arylsulfonyl group (preferably a substituted or unsubstituted alkylsulfonyl group having 1 to 30 carbon atoms or arylsulfonyl group having 6 to 30 carbon atoms, for example, methylsulfonyl, ethylsulfonyl, phenylsulfonyl and p-methylphenylsulfonyl), acyl group (preferably a formyl group, a substituted or unsubstituted alkylcarbonyl group having 2 to 30 carbon atoms, substituted or unsubstituted arylcarbonyl group having 7 to 30 carbon atoms or heterocyclic carbonyl group which has 4 to 30 carbon atoms and in which the ring is combined with the carbonyl group through a carbon atom, for example, acetyl, pivaloyl, 2-chloroacetyl, stearoyl, benzoyl, p-n-octyloxyphenylcarbonyl, 2-pyridylcarbonyl and 2-furylcarbonyl), aryloxycarbonyl group (preferably a substituted or unsubstituted aryloxycarbonyl group having 7 to 30 carbon atoms, for example, phenoxycarbonyl, o-chlorophenoxycarbonyl, m-nitrophenoxycarbonyl and p-t-butylphenoxycarbonyl), alkoxycarbonyl group (preferably a substituted or unsubstituted alkoxycarbonyloxy group having 2 to 30 carbon atoms, for example, methoxycarbonyl, ethoxycarbonyl, t-butoxycarbonyl and n-octadecyloxycarbonyl), carbamoyl group (preferably a substituted or unsubstituted carbamoyl group having 1 to 30 carbon atoms, for example, carbamoyl, N-methylcarbamoyl, N,N-dimethylcarbamoyl, N,N-di-n-octylcarbamoyl and N-(methylsulfonyl)carbamoyl), aryl or heterocyclic azo group (preferably a substituted or unsubstituted aryl azo group having 6 to 30 carbon atoms or heterocyclic azo group having 3 to 30 carbon atoms, for example, phenylazo, p-chlorophenylazo and 5-ethylthio-1,3,4-thiadiazole-2-ylazo), imide group (preferably N-succinimide and N-phthalimide), phosphino group (preferably a substituted or unsubstituted phosphino group having 2 to 30 carbon atoms, for example, dimethylphosphino, diphenylphosphino and methylphenoxyphosphino), phosphinyl group (preferably a substituted or unsubstituted phosphinyl group having 2 to 30 carbon atoms, for example, phosphinyl, dioctyloxyphosphinyl and diethoxyphosphinyl), phosphinyloxy group (preferably a substituted or unsubstituted phosphinyloxy group having 2 to 30 carbon atoms, for example, diphenoxyphosphinyloxy and dioctyloxyphosphinyloxy), phosphinylamino group (preferably a substituted or unsubstituted phosphinylamino group having 2 to 30 carbon atoms, for example, dimethoxyphosphinylamino and dimethylaminophosphinylamino) and silyl group (preferably a substituted or unsubstituted silyl group having 3 to 30 carbon atoms, for example, trimethylsilyl, t-butyldimethylsilyl and phenyldimethylsilyl).

Among the above functional groups, those having a hydrogen atom may be removed and further substituted with the above group. Examples of such a functional group include an alkylcarbonylaminosulfonyl group, arylcarbonylaminosulfonyl group, alkylsulfonylaminocarbonyl group and arylsulfonylaminocarbonyl group. Specific examples of these groups include methylsulfonylaminocarbonyl, p-methylphenylsulfonylaminocarbonyl, acetylaminosulfonyl and benzoylaminosulfonyl.

Examples of the substituent of the aryl part of the substituted aralkyl group are the same as the examples of the substituent of the following substituted aryl group.

In the specification, the aromatic group means an aryl group or a substituted aryl group. These aromatic groups may be condensed with aliphatic rings, other aromatic rings or hetero rings. The number of carbon atoms of the aromatic group is preferably 6 to 40, more preferably 6 to 30, and still more preferably 6 to 20. Among these groups, the aryl group is preferably phenyl or naphthyl, and particularly preferably phenyl.

The aryl part of the substituted aryl group is the same as that of the above aryl group. Examples of the substituent of the substituted aryl group are the same as those given as the examples of the substituent of the alkyl part of the above-mentioned substituted alkyl group, substituted alkenyl group, substituted alkinyl group and substituted aralkyl group.

In the specification, the hetero ring in the heterocyclic group preferably include a five- or six-membered saturated or unsaturated hetero ring. This hetero ring may be condensed with aliphatic rings, aromatic rings or other hetero rings. Examples of the hetero atom of the hetero ring include B, N, O, S, and Se, and Te. N, O or S is preferable as the hetero atom. The hetero ring preferably contains a carbon atom having a free atomic valence (monovalent) (the heterocyclic group is combined through the carbon atom). The number of atoms of the heterocyclic group is preferably 1 to 40, more preferably 1 to 30 and still more preferably 1 to 20. Examples of the saturated hetero ring in the heterocyclic group include a pyrrolidine ring, morpholine ring, 2-bora-1,3-dioxolan ring and 1,3-thiazolidine ring. Examples of the unsaturated hetero ring in the heterocyclic group include an imidazole ring, thiazole ring, benzothiazole ring, benzoxazole ring, benzotriazole ring, benzoselenazole ring, pyridine ring, pyrimidine ring and quinoline ring. The heterocyclic group may have a substituent. Examples of the substituent are the same as those given as the examples of the substituent of the alkyl part of the above-mentioned substituted alkyl group, substituted alkenyl group, substituted alkinyl group and substituted aralkyl group.

Next, the compounds represented by the formulae (1) to (6) will be explained.

In the formulae (1) to (3), $R^{11}$ represents a hydrogen atom, an aliphatic group, an aromatic group or a heterocyclic group. These groups are the same as mentioned-above. $R^{11}$ is preferably an aliphatic group or an aromatic group, and more preferably an aliphatic group having 1 to 40 carbon atoms, an aromatic group having 6 to 40 carbon atoms or an aromatic group having 3 to 40 carbon atoms. $R^{11}$ is still more preferably an aliphatic group having 1 to 30 carbon atoms or an aromatic group having 6 to 30 carbon atoms, even more preferably an aliphatic group having 1 to 30 carbon atoms, and most preferably an aliphatic group which forms a conjugate double bond with amide carbonyl or ester carbonyl where the α- and β-positions of the amide or ester carbonyl group are double bonds.

$R^{12}$ and $R^{13}$ each independently represent a hydrogen atom, an aliphatic group, an aromatic group or a heterocyclic group, where these groups are the same as above-mentioned. However, $R^{12}$ and $R^{13}$ are not each independently a hydrogen atom at the same time. $R^{12}$ and $R^{13}$ are each independently preferably a hydrogen atom, an aliphatic group or an aromatic group. It is more preferable that $R^{12}$ is a hydrogen atom and $R^{13}$ is an aliphatic group or an aromatic group. It is still more preferable that $R^{13}$ is an aliphatic group having 1 to 30 carbon atoms or an aromatic group having 6 to 30 carbon atoms. It is even more preferable that $R^{13}$ be an aromatic group having 6 to 20 carbon atoms. $R^{13}$ is most preferably a phenyl group having a substituent at the ortho-position with respect to an amino group.

$R^{21}$ represents an aliphatic group, an aromatic group or a heterocyclic group where these groups are the same as above-mentioned. $R^{21}$ is preferably an aliphatic group having 1 to 10 carbon atoms, an aromatic group having 6 to 15 carbon atoms or a heterocyclic group having 3 to 10 carbon atoms, more preferably an aliphatic group having 1 to 6 carbon atoms or an aromatic group having 6 to 10 carbon atoms, still more preferably an aliphatic or aromatic group unsubstituted or substituted with a halogen atom. $R^{21}$ is most preferably an aliphatic group having 1 to 4 carbon atoms.

In the formulae (4) to (6), $R^{41}$ represents a substituent. Examples of the substituent are the same as those given as the examples of the substituent of the alkyl part of the above-mentioned substituted alkyl group, substituted alkenyl group, substituted alkinyl group and substituted aralkyl group. Preferable examples of $R^{41}$ include a halogen atom, alkyl group, alkenyl group, alkinyl group, aryl group, heterocyclic group, hydroxyl group, alkoxy group, aryloxy group, silyloxy group, heterocyclic oxy group, alkylthio group, arylthio group, heterocyclic thio group, alkyl or arylsulfinyl group, alkyl or arylsulfonyl group, phosphino group, phosphinyl group, phosphinyloxy group and silyl group. More preferable examples of $R^{41}$ include a halogen atom, alkyl group, alkenyl group, aryl group, heterocyclic group, alkoxy group, aryloxy group, silyloxy group, alkylthio group, arylthio group and silyl group. Still more preferable examples of $R^{41}$ include a fluorine atom, chlorine atom, alkyl group having 1 to 5 carbon atoms, aryl group having 6 to 10 carbon atoms, heterocyclic group having 3 to 5 carbon atoms, alkoxy group having 1 to 5 carbon atoms, aryloxy group having 6 to 10 carbon atoms, silyloxy group having 3 to 6 carbon atoms, alkylthio group having 1 to 5 carbon atoms, arylthio group having 6 to 10 carbon atoms and silyl group having 3 to 6 carbon atoms. Even more preferable examples of $R^{41}$ include a fluorine atom, chlorine atom, alkyl group having 1 to 4 carbon atoms, aryl group having 6 to 8 carbon atoms, alkoxy group having 1 to 4 carbon atoms and alkylthio group having 1 to 5 carbon atoms. These functional groups may further have a substituent. Examples of the substituent are the same as those given as the examples of the substituent of the alkyl part of the above-mentioned substituted alkyl group, substituted alkenyl group, substituted alkinyl group and substituted aralkyl group.

No particular limitation is imposed on the substituted position of $R^{41}$ on the benzene ring.

$R^{42}$ represents a hydrogen atom, an aliphatic group, an aromatic group or a heterocyclic group and is preferably a hydrogen atom or an aliphatic group, and more preferably an aliphatic group having 1 to 30 carbon atoms. $R^{42}$ is still more preferably an alkyl group having 1 to 20 carbon atoms or an aralkyl group, and most preferably an alkyl group having 1 to 20 carbon atoms. The alkyl group and aralkyl group may have a substituent. Examples of the substituent are the same as those given as the examples of the substituent of the alkyl part of the above-mentioned substituted alkyl group and substituted aralkyl group.

$R^{43}$ represents a hydrogen atom, an aliphatic group, an aromatic group or a heterocyclic group, and is preferably a hydrogen atom or an aliphatic group, and more preferably a hydrogen atom or an alkyl group having 1 to 5 carbon atoms. The alkyl group may have a substituent. Examples of the substituent are the same as those given as the examples of the substituent of the above-mentioned substituted alkyl group.

$R^{43}$ is most preferably a hydrogen atom.

$R^{44}$ represents a hydrogen atom, an aliphatic group, an aromatic group or a heterocyclic group and is preferably a hydrogen atom or an aliphatic group, and more preferably a hydrogen atom or an alkyl group having 1 to 5 carbon atoms, an aromatic group having 6 to 10 carbon atoms or a heterocyclic group having 3 to 5 carbon atoms. $R^{44}$ is still more preferably a hydrogen atom, an alkyl group having 1 to 3 carbon atoms or an aromatic group having 6 to 8 carbon atoms. The alkyl group may have a substituent. Examples of the substituent are the same as those given as the examples of the substituent of the above-mentioned substituted alkyl group.

$R^{44}$ is most preferably a hydrogen atom.

$R^{45}$ represents a substituent. Examples of the substituent include those exemplified as the substituent of the alkyl part of the above-mentioned substituted alkyl group, substituted alkenyl group, substituted alkinyl group or substituted aralkyl group. $R^{45}$ is preferably a halogen atom, alkyl group, alkenyl group, alkinyl group, aryl group, heterocyclic group, hydroxyl group, alkoxy group, aryloxy group, silyloxy group, heterocyclic oxy group, alkylthio group, arylthio group, heterocyclic thio group, alkyl or arylsulfinyl group, alkyl or arylsulfonyl group, phosphino group, phosphinyl group, phosphinyloxy group and silyl group, more preferably an alkyl group, aryl group, heterocyclic group, alkoxy group, aryloxy group, silyloxy group, alkylthio group, arylthio group and silyl group, still more preferably an alkyl group having 1 to 15 carbon atoms, aryl group having 6 to 10 carbon atoms, heterocyclic group having 3 to 5 carbon atoms, alkoxy group having 1 to 5 carbon atoms, aryloxy group having 6 to 10 carbon atoms, silyloxy group having 3 to 6 carbon atoms, alkylthio group having 1 to 10 carbon atoms, arylthio group having 6 to 10 carbon atoms and silyl group having 3 to 6 carbon atoms, and even more preferably an alkyl group having 1 to 10 carbon atoms, alkoxy group having 1 to 4 carbon atoms and alkylthio group having 1 to 10 carbon atoms. These functional groups may further have a substituent. Examples of the substituent include the same ones as those given as the examples of the substituent of the alkyl part of the above-mentioned substituted alkyl group, substituted alkenyl group, substituted alkinyl group and substituted aralkyl group.

$R^{51}$ represents an aliphatic group, an aromatic group or a heterocyclic group, and is preferably an aliphatic group or an aromatic group, more preferably an aliphatic group having 1 to 8 carbon atoms or an aromatic group having 6 to 10 carbon atoms, still more preferably an alkyl group having 1 to 4 carbon atoms or a phenyl group, and most preferably an alkyl group having 1 to 4 carbon atoms. The alkyl group and phenyl group may further have a substituent. Examples of the substituent include the same ones as those given as the examples of the substituent of the alkyl part of the above-mentioned substituted alkyl group, substituted alkenyl group, substituted alkinyl group and substituted aralkyl group.

$n^{41}$ denotes an integer from 0 to 4 and is preferably an integer from 0 to 2, more preferably an integer from 0 to 1, and most preferably 0.

$n^{45}$ denotes an integer from 0 to 5 and is preferably an integer from 0 to 3, and more preferably an integer from 0 to 2.

Specific examples of the compounds represented by the formula (4) or (5) will be shown below. The chemical structure shows one of tautomers (tautomerism based on movement of a π electron and a hydrogen atom) and the invention includes these tautomers.

Next, specific examples of the compounds represented by the formula (1) or (4) will be given below: however, these examples are not intended to be limiting of the invention.

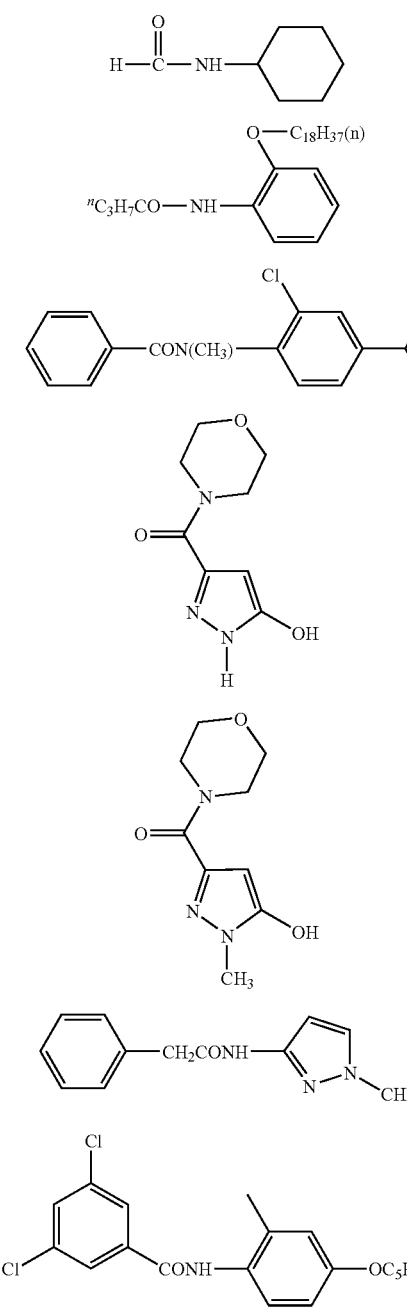

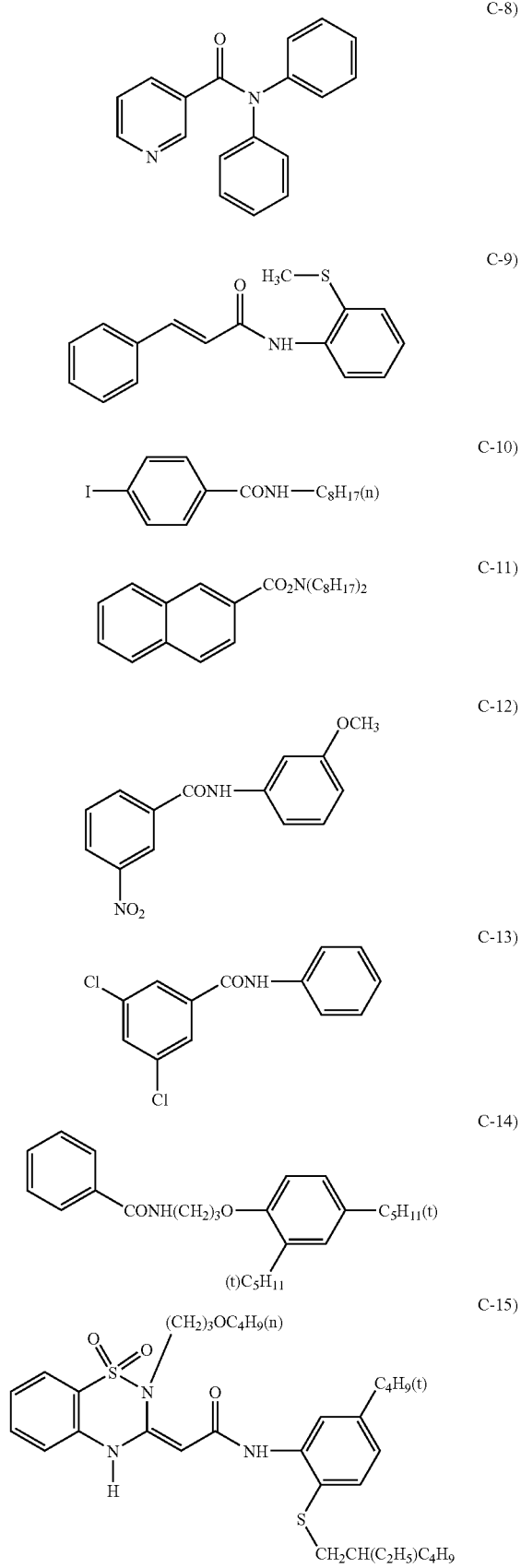

-continued
C-16)
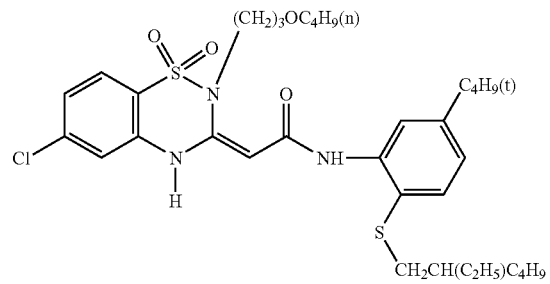
C-17)
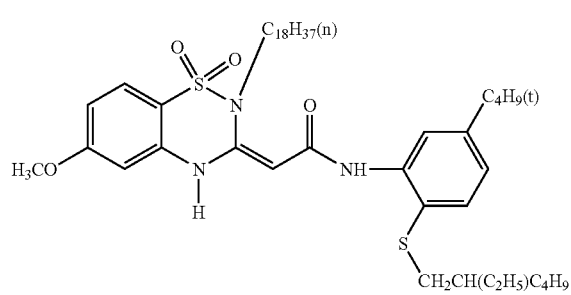
C-18)
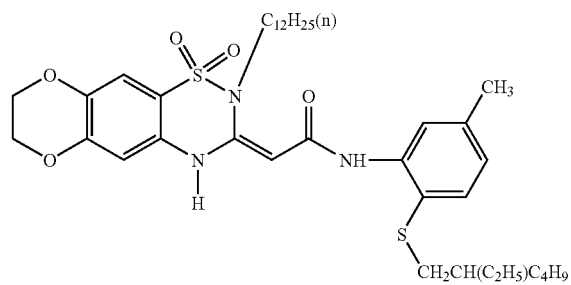
C-19)
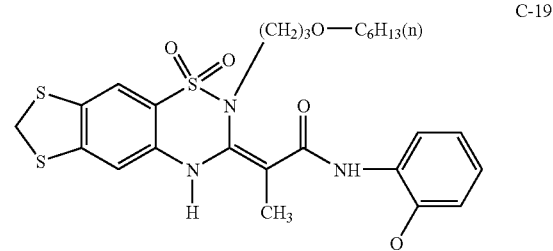
C-20)
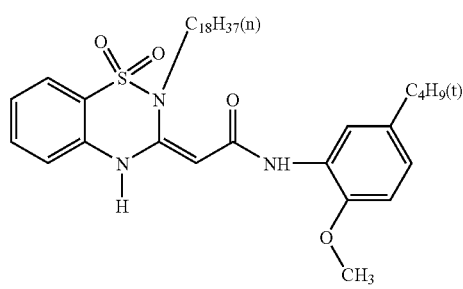
-continued
C-21)
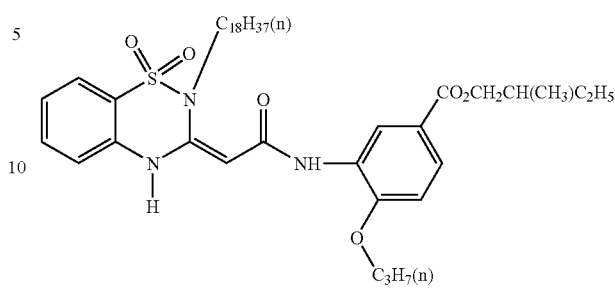
C-22)
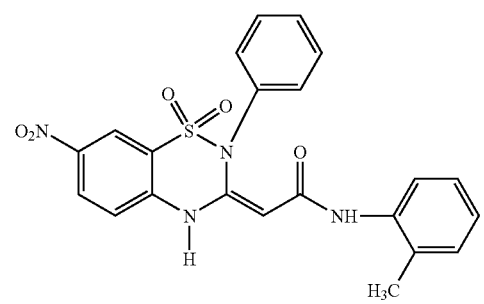
C-23)
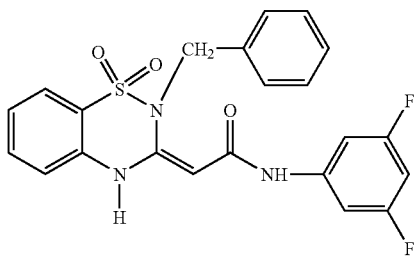
C-24)
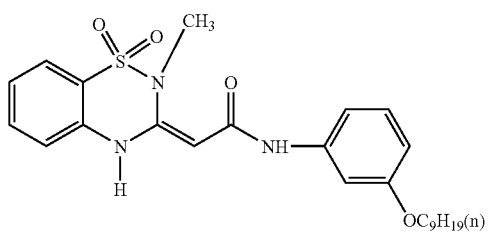
C-25)
C-26)
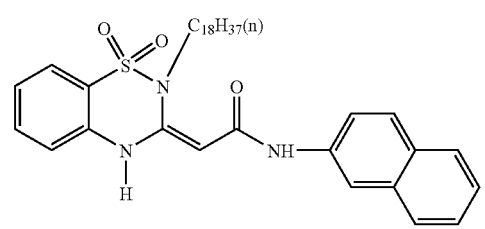

-continued
C-27)
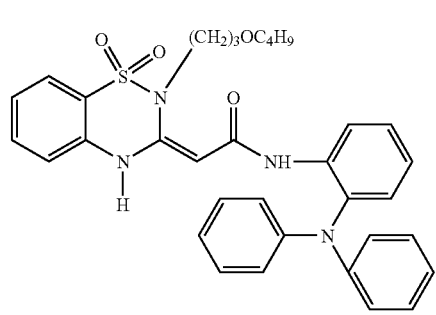
C-28)
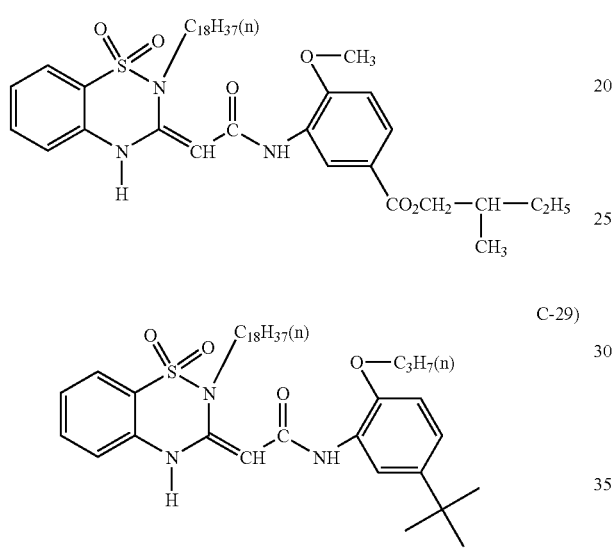
C-29)
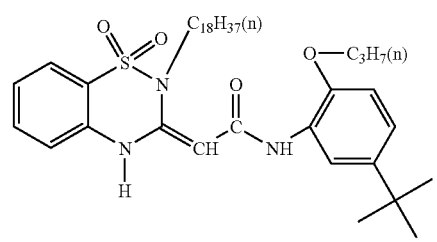
Next, specific examples of the compounds represented by the formula (2) or (5) will be given below: however, these examples are not intended to be limiting of the invention.
E-1)
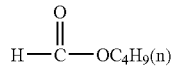
E-2)
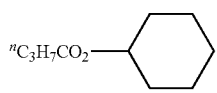
E-3)
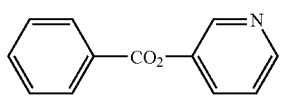
E-4)
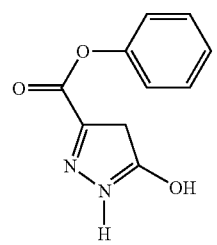
E-5)
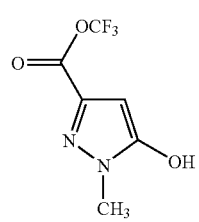
E-6)
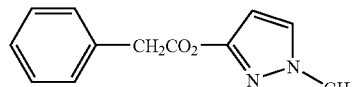
E-7)
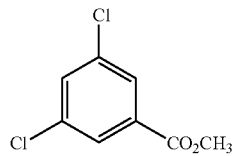
E-8)
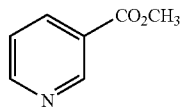
E-9)
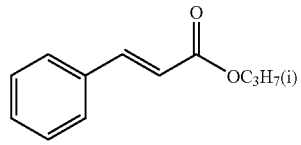
E-10)
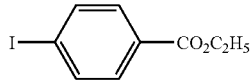
E-11)
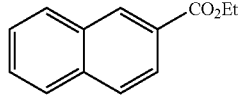
E-12)
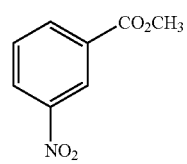
E-13)
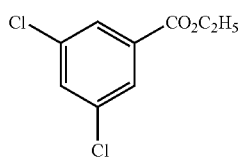
E-14)
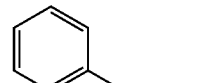
E-15)
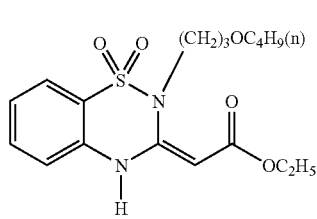

-continued
E-16)
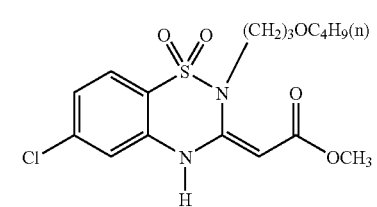
E-17)
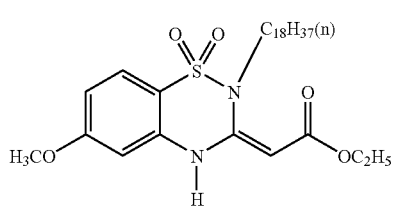
E-18)
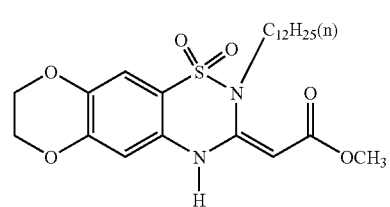
E-19)
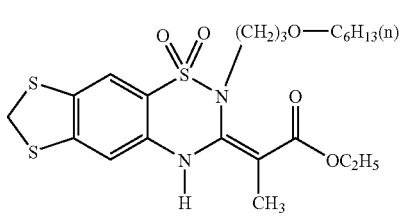
E-20)
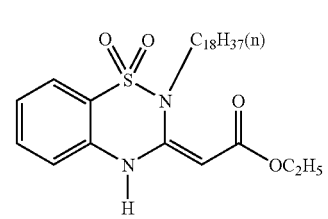
E-21)
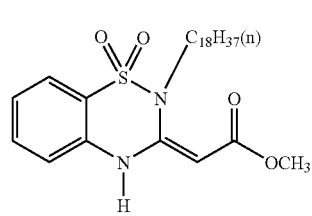
E-22)
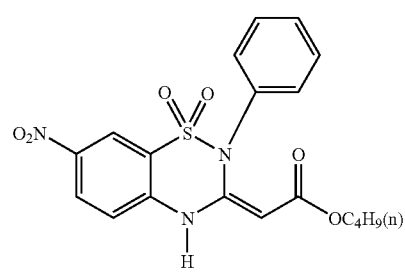
-continued
E-23)
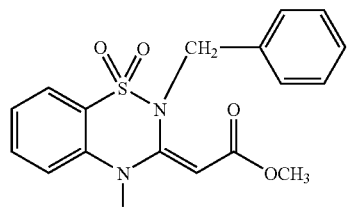
E-24)
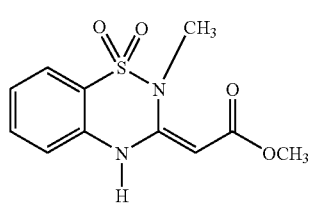
E-25)
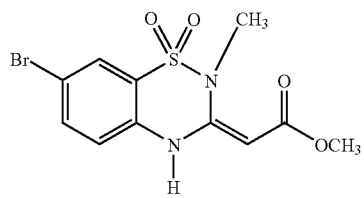
E-26)
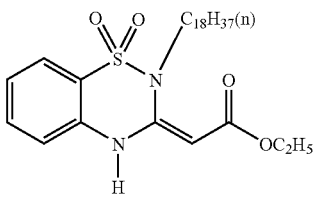
E-27)
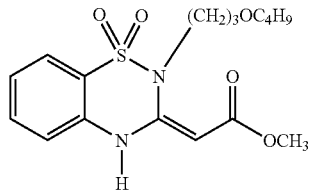
Next, specific examples of the compounds represented by the formula (3) or (6) will be given below: however, these examples are not intended to be limiting of the invention.
A-1)
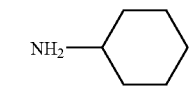
A-2)
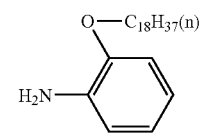
A-3)
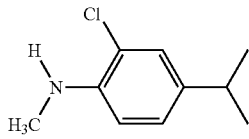

-continued
A-4) 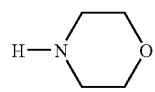
A-5) 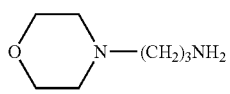
A-6) 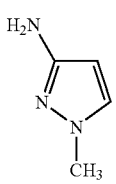
A-7) 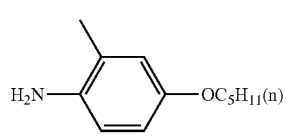
A-8) 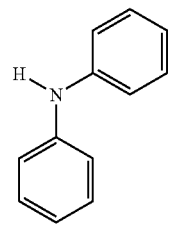
A-9) 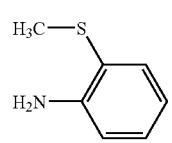
A-10) $^nC_8H_{17}NH_2$
A-11) $(^nC_8H_{17})_2NH$
A-12) 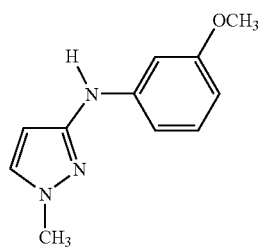
A-13) 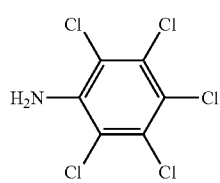
A-14) 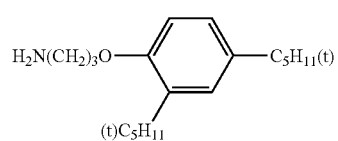
-continued
A-15) 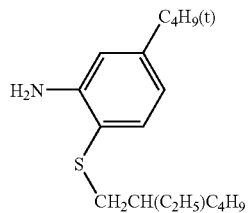
A-16) 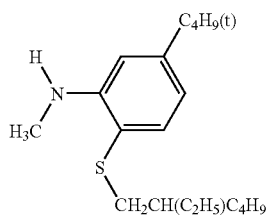
A-17) 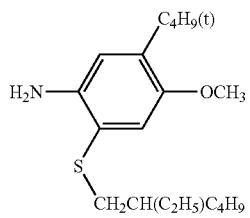
A-18 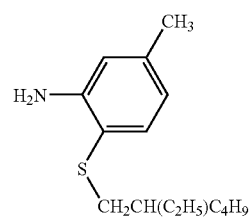
A-19) 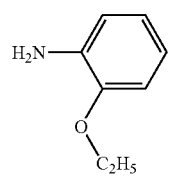
A-20) 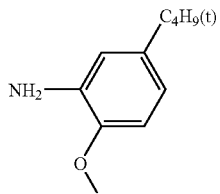
A-21) 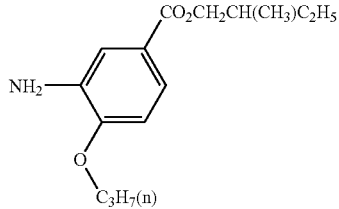

-continued

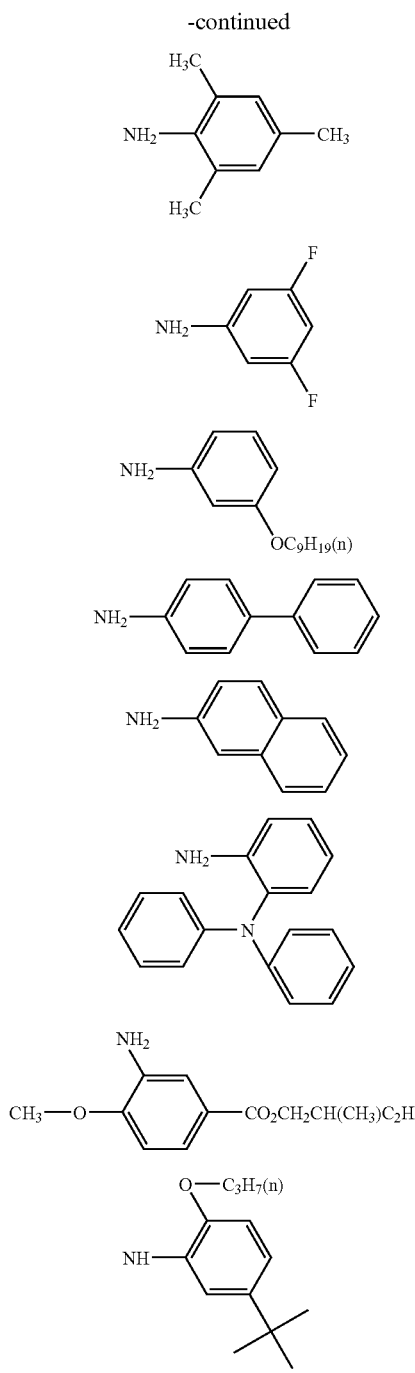

A-22)
A-23)
A-24)
A-25)
A-26)
A-27)
A-28)
A-29)

Examples of the aluminum alkoxide compound in the invention include aluminum methoxide, aluminum ethoxide, aluminum-n-propoxide, aluminum isopropoxide and aluminum-t-butoxide. Among these compounds, aluminum isopropoxide is the most preferable.

These compounds may be used either singly or in combinations of two or more and also in combination with other metal compounds. These other metal compounds to be combined are compounds containing III to XVI group metals, preferably III to V group metals, XII to XIII group metals and a lanthanoid type, for example, aluminum (III) chloride, titanium (IV) chloride, vanadium (V) chloride, lanthanum (III) chloride, hafnium (IV) chloride and zirconium (IV) chloride.

The reaction for obtaining the compound represented by the formula (1) or (4) is carried out using the compound represented by the formula (2) or (5), the compound represented by the formula (3) or (6), and an aluminum alkoxide compound in the presence of a solvent or no solvent.

As the solvent, for example, an amide type solvent (e.g., N,N-dimethylformamide, N,N-dimethylacetamide and 1-methyl-2-pyrrolidone), sulfone type solvent (e.g., sulfolane), sulfoxide type solvent (e.g., dimethylsulfoxide), ureide type solvent (e.g., tetramethylurea), ether type solvent (e.g., dioxane), ketone type solvent (e.g., acetone and cyclohexanone), hydrocarbon type solvent (e.g., toluene, xylene, mesitylene, n-octane and n-decane) and halogen type solvent (e.g., tetrachloroethane, chlorobenzene and dichlorobenzene) may be used either independently or in combinations of two or more.

In a preferable case, no solvent, a hydrocarbon type solvent or a halogen type solvent is used, and in a more preferable case, no solvent or a hydrocarbon type solvent is used.

The reaction is carried out at a temperature of 30 to 250° C., preferably 80 to 200° C. and more preferably 100 to 170° C. for a reaction time range from 5 minutes to 30 hours.

It is preferable to remove by-produced alcohols during reaction. For this, a method in which these alcohols are removed under reduced pressure or normal pressure either singly or together with a solvent, a method of using an absorber such as a molecular sieve or a method of impregnating an inorganic salt with these alcohols as a crystal solvent is preferably used.

As to the molar ratio of raw materials to be used in the reaction, the ratio of the compound represented by the formula (3) or (6) to the compound represented by the formula (2) or (5) is preferably 0.8 to 1.20 mol, more preferably 0.85 to 1.15 mol, still more preferably 0.90 to 1.10 mol, and most preferably 0.95 to 1.05 mol based on 1 mol of the compound represented by the formula (2) or (5). Conventionally, in the case of synthesizing an amide compound from an ester compound, a more inexpensive raw material among the ester compound and an amine compound is excessively used whereas in the invention, the reaction proceeds quantitatively or nearly quantitatively, which is very economical.

The amount of the aluminum alkoxide compound is preferably 2.0 mol or less, more preferably 1.0 mol or less, still more preferably 0.5 mol or less, and most preferably 0.1 mol or less based on 1 mol of the compound represented by the formula (2) or (5). The lower limit of the amount is preferably 0.000001 mol or more. Even if the aluminum alkoxide compound is used in an amount of 2.0 mol or more, reaction yield is not improved and also, it is troublesome to remove aluminum compounds from the reaction system after the reaction. Therefore, the amount of the aluminum alkoxide compound is preferably 2.0 mol or less in the invention.

EXAMPLES

The present invention will be explained in more detail by way of examples, which are, however, not intended to be limiting of the invention.

Example 1

The exemplified compound (C-15) was synthesized based on the following reaction scheme.

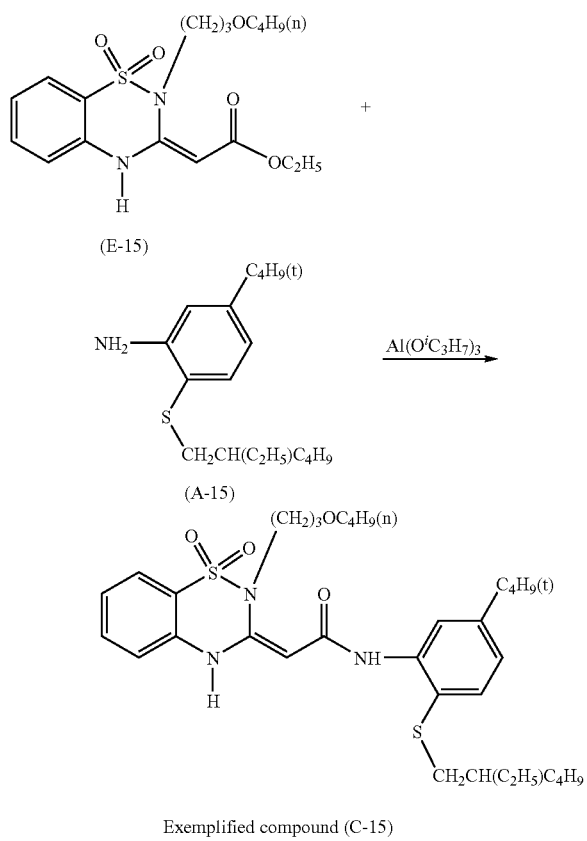

Exemplified compound (C-15)

A three-neck flask was charged with 38.2 g of the compound (E-15), 32.3 g of the compound (A-15) and 20.4 g of aluminum isopropoxide and the mixture was reacted at an internal temperature of 110 to 150° C. under reduced pressure of 1 mm Hg for 12 hours with stirring while a produced ethanol by-produced was removed. After the reaction mixture was cooled to room temperature, 500 ml of ethyl acetate, 400 g of ice, 43 ml of hydrochloric acid and 100 ml of saturated brine were added to the reaction mixture to carry out extraction. The resulting ethyl acetate phase was washed with a mixed solvent of 400 ml of water and 100 ml of saturated brine four times. A residue obtained by concentrating the thus obtained ethyl acetate phase by a rotary evaporator was purified using silica gel chromatography to obtain 58.6 g (yield: 93%) of the intended exemplified compound (C-15). The compound was identified by $^1$H-NMR (solvent: CDCl$_3$) and mass spectrum. Products obtained in the following examples were identified by the same method.

Example 2

A three-neck flask was charged with 38.2 g of the compound (E-15), 30.8 g of the compound (A-15) and 2.0 g of aluminum isopropoxide and the mixture was reacted at an internal temperature of 110 to 150° C. under reduced pressure of 1 mm Hg for 12 hours with stirring while by-produced ethanol was removed. After that, 100 ml of mesitylene was added to the reaction mixture, which was then further stirred to distill mesitylene. At this time, the ultimate vacuum was 2 mm Hg and the ultimate internal temperature was 135° C. After the reaction mixture was cooled to room temperature, 500 ml of ethyl acetate, 400 g of ice, 43 ml of hydrochloric acid and 100 ml of saturated brine were added to the reaction mixture to carry out extraction. The resulting ethyl acetate phase was washed with a mixed solvent of 400 ml of water and 100 ml of saturated brine four times. A residue obtained by concentrating the thus obtained ethyl acetate phase by a rotary evaporator was purified using silica gel chromatography to obtain 58.0 g (yield: 92%) of the intended exemplified compound (C-15).

Example 3

A three-neck flask was charged with 38.2 g of the compound (E-15), 30.8 g of the compound (A-15), 2.0 g of aluminum isopropoxide and 500 ml of xylene and the mixture was reacted at an internal temperature of 100 to 160° C. under reduced pressure of 200 to 350 mm Hg for 12 hours with stirring while removing by-produced ethanol and xylene. After the reaction mixture was cooled to room temperature, 500 ml of ethyl acetate, 400 g of ice, 43 ml of hydrochloric acid and 100 ml of saturated brine were added to the reaction mixture to carry out extraction. The resulting ethyl acetate phase was washed with a mixed solvent of 400 ml of water and 100 ml of saturated brine four times. A residue obtained by concentrating the thus obtained ethyl acetate phase by a rotary evaporator was purified using silica gel chromatography to obtain 59.8 g (yield: 95%) of the intended exemplified compound (C-15).

Example 4

The exemplified compound (C-21) of the invention was synthesized according to the following reaction scheme.

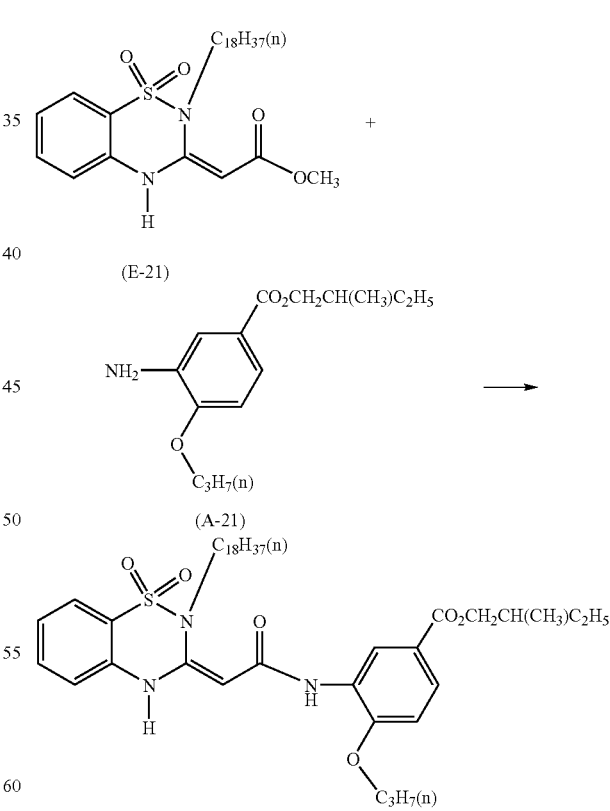

Exemplified compound (C-21)

A three-neck flask was charged with 52.1 g of the compound (E-21), 27.9 g of the compound (A-21) and 6.0 g of aluminum isopropoxide and the mixture was reacted at an internal temperature of 120 to 155° C. under reduced pressure of 1 mm Hg for 12 hours with stirring while by-produced ethanol was removed. After that, 100 ml of mesitylene was added to the reaction mixture, which was then further stirred to distill mesitylene. At this time, the ultimate vacuum was 2 mm Hg and the ultimate internal temperature was 140° C. After the reaction mixture was cooled to room temperature, 500 ml of ethyl acetate, 400 ml of water and 100 ml of saturated brine were added to the reaction mixture to carry out extraction. The resulting ethyl acetate phase was washed with a mixed solvent of 400 ml of water and 100 ml of saturated brine four times. A residue obtained by concentrating the thus obtained ethyl acetate phase by a rotary evaporator was purified using silica gel chromatography to obtain 68.8 g (yield: 93%) of the intended exemplified compound (C-21).

Example 5

The exemplified compound (C-14) of the invention was synthesized according to the following reaction scheme.

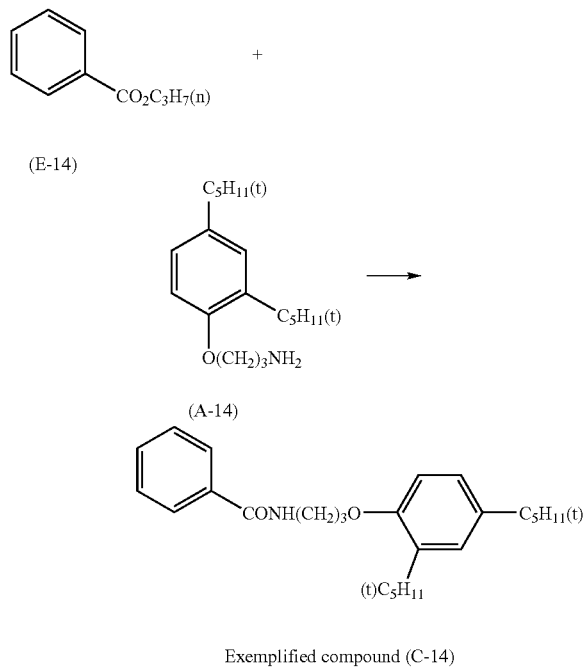

A three-neck flask was charged with 16.4 g of the compound (E-14), 30.3 g of the compound (A-14) and 6.0 g of aluminum isopropoxide and the mixture was reacted at an internal temperature of 110 to 145° C. under reduced pressure of 1 mm Hg for 8 hours with stirring while by-produced ethanol was removed. After the reaction mixture was cooled to room temperature, 500 ml of ethyl acetate, 400 g of ice, 43 ml of hydrochloric acid and 100 ml of saturated brine were added to the reaction mixture to carry out extraction. The resulting ethyl acetate phase was washed with a mixed solvent of 400 ml of water and 100 ml of saturated brine four times. A residue obtained by concentrating the thus obtained ethyl acetate phase by a rotary evaporator was purified using silica gel chromatography to obtain 34.2 g (yield: 90%) of the intended exemplified compound (C-14).

Example 6

The exemplified compound (C-28) of the invention was synthesized according to the following reaction scheme.

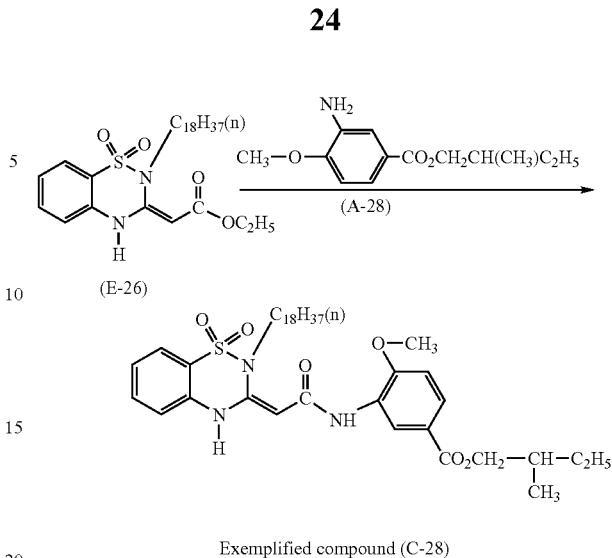

A three-neck flask was charged with 52.1 g of the compound (E-26), 24.9 g of the compound (A-28), 4.0 g of aluminum isopropoxide and 500 ml of xylene and the mixture was reacted at an internal temperature of 105 to 155° C. under reduced pressure of 200 to 350 mm Hg for 11 hours with stirring while removing by-produced ethanol and xylene. After the reaction mixture thus obtained was cooled to room temperature, 500 ml of ethyl acetate, 400 g of ice, 43 ml of hydrochloric acid and 100 ml of saturated brine were added to the reaction mixture to carry out extraction. The resulting ethyl acetate phase was washed with a mixed solvent of 400 ml of water and 100 ml of saturated brine four times. A residue obtained by concentrating the thus obtained ethyl acetate phase by a rotary evaporator was purified using silica gel chromatography to obtain 66.9 g (yield: 94%) of the intended exemplified compound (C-28).

Example 7

The exemplified compound (C-29) of the invention was synthesized according to the following reaction scheme.

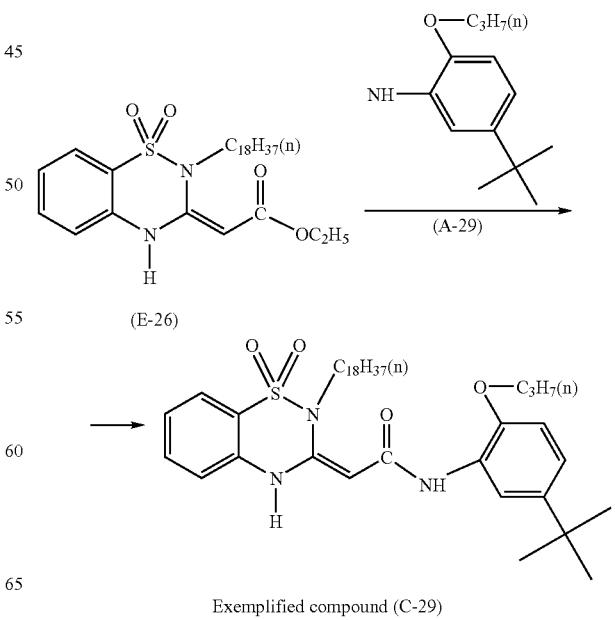

A three-neck flask was charged with 52.1 g of the compound (E-26), 21.8 g of the compound (A-29), 2.0 g of aluminum isopropoxide and 500 ml of xylene and the mixture was reacted at an internal temperature of 105 to 155° C. under reduced pressure of 200 to 350 mm Hg for 12 hours with stirring while removing by-produced ethanol and xylene. After the reaction mixture thus obtained was cooled to room temperature, 500 ml of ethyl acetate, 400 g of ice, 43 ml of hydrochloric acid and 100 ml of saturated brine were added to the reaction mixture to carry out extraction. The resulting ethyl acetate phase was washed with a mixed solvent of 400 ml of water and 100 ml of saturated brine four times. A residue obtained by concentrating the thus obtained ethyl acetate phase by a rotary evaporator was purified using silica gel chromatography to obtain 65.5 g (yield: 96%) of the intended exemplified compound (C-29).

Comparative Example 1

A three-neck flask was charged with 38.2 g of the compound (E-15) and 32.3 g of the compound (A-15) and the mixture was reacted at an internal temperature of 115 to 150° C. under reduced pressure of 1 mmHg for 12 hours with stirring while removing by-produced ethanol. After the reaction mixture thus obtained was cooled to room temperature, 500 ml of ethyl acetate, 400 g of ice, 43 ml of hydrochloric acid and 100 ml of saturated brine were added to the reaction mixture to carry out extraction. The resulting ethyl acetate phase was washed with a mixed solvent of 400 ml of water and 100 ml of saturated brine four times. A residue obtained by concentrating the thus obtained ethyl acetate phase by a rotary evaporator was purified using silica gel chromatography to obtain 15.7 g (yield: 25%) of the intended exemplified compound (C-15).

Comparative Example 2

A three-neck flask was charged with 16.4 g of the compound (E-14) and 30.3 g of the compound (A-14) and the mixture was reacted at an internal temperature of 110 to 145° C. under reduced pressure of 1 mmHg for 12 hours with stirring while removing by-produced methanol. After the reaction mixture thus obtained was cooled to room temperature, 500 ml of ethyl acetate, 400 g of ice, 43 ml of hydrochloric acid and 100 ml of saturated brine were added to the reaction mixture to carry out extraction. The resulting ethyl acetate phase was washed with a mixed solvent of 400 ml of water and 100 ml of saturated brine four times. A residue obtained by concentrating the thus obtained ethyl acetate phase by a rotary evaporator was purified using silica gel chromatography to obtain 18.2 g (yield: 48%) of the intended exemplified compound (C-14).

What is claimed is:

1. A method of producing a compound represented by the following formula (4) or a tautomer thereof, the process comprising reacting a compound represented by the following formula (5) or a tautomer thereof with a compound represented by the following formula (6) in the presence of an aluminum alkoxide compound:

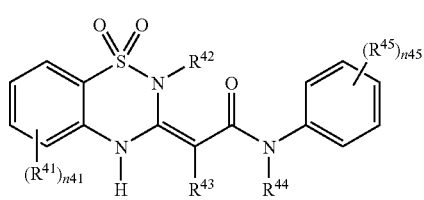

Formula (4)

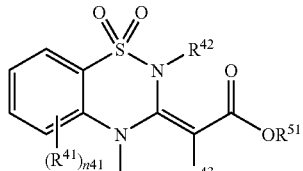

Formula (5)

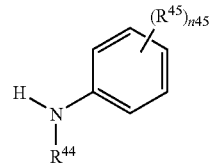

Formula (6)

wherein $R^{41}$ and $R^{45}$ each independently represent a substituent selected from the group consisting of:
an alkyl group, an alkenyl group, an alkinyl group, an aralkyl group, an aryl group, a heterocyclic group, a halogen atom, a hydroxyl group, an alkoxy group, an aryloxy group, a silyloxy group, a heterocyclic oxy group, an alkylthio group, an arylthio group, a heterocyclic thio group, an alkylsulfinyl group, an arysulfinyl group, an alkylsulfonyl group, an arysulfonyl group, a phosphino group, a phosphinyl group, a phosphinyloxy group, and a silyl group;

$R^{42}$, $R^{43}$ and $R^{44}$ each independently represent a hydrogen atom, an aliphatic group, an aromatic group or a heterocyclic group; $R^{51}$ represents an aliphatic group, an aromatic group or a heterocyclic group; $n^{41}$ denotes an integer from 0 to 4; $n^{45}$ denotes an integer from 0 to 5; when $n^{41}$ is 2 or more, plural $R^{41}$s may be the same or different and may be combined with each other to form a ring; and when $n^{45}$ is 2 or more, plural $R^{45}$s may be the same or different and may be combined with each other to form a ring.

2. The method according to claim 1, wherein the amount of the compound represented by formula (6) is 0.8 to 1.2 mol based on 1 mol of the compound represented by formula (5) or the tautomer thereof 3. The method according to claim 1, wherein the aluminum alkoxide compound is aluminum isopropoxide.

4. The method according to claim 2, wherein the aluminum alkoxide compound is aluminum isopropoxide.

5. The method according to claim 1, wherein $R^{42}$ is an alkyl group having 1 to 20 carbon atoms.

6. The method according to claim 1, wherein $R^{43}$ is a hydrogen atom.

7. The method according to claim 1, wherein $R^{44}$ is a hydrogen atom.

8. The method according to claim 1, wherein $R^{51}$ is an alkyl group having 1 to 4 carbon atoms.

9. The method according to claim 1, wherein the reaction is carried out without a solvent or with a hydrocarbon type solvent.

10. The method according to claim 1, wherein the amount of the aluminum alkoxide compound is 0.1 mol or less based on 1 mol of the compound represented by formula (5).

* * * * *